(12) United States Patent
Reed

(10) Patent No.: US 8,602,781 B2
(45) Date of Patent: Dec. 10, 2013

(54) DENTAL IMPLANT WITH INTERLOCKING AND CENTERING THREADS

(76) Inventor: Gary J. Reed, Turlock, CA (US)

( * ) Notice: Subject to any disclaimer, the term of this patent is extended or adjusted under 35 U.S.C. 154(b) by 753 days.

(21) Appl. No.: 11/749,709

(22) Filed: May 16, 2007

(65) Prior Publication Data

US 2008/0286720 A1    Nov. 20, 2008

(51) Int. Cl.
*A61C 8/00* (2006.01)
*A61B 17/76* (2006.01)
*F16B 35/00* (2006.01)

(52) U.S. Cl.
USPC ............................. 433/174; 606/301; 411/411

(58) Field of Classification Search
USPC .............. 433/167, 172–176, 215; 606/65, 66, 606/300–320; 411/16, 17, 39, 387, 394, 411/395, 393, 411–426
See application file for complete search history.

(56) References Cited

U.S. PATENT DOCUMENTS

| | | | | |
|---|---|---|---|---|
| 2,112,007 A | * | 3/1938 | Adams | 433/174 |
| 4,086,701 A | * | 5/1978 | Kawahara et al. | 433/174 |
| 4,144,795 A | * | 3/1979 | Gutshall | 411/413 |
| 4,334,814 A | * | 6/1982 | McKewan | 411/311 |
| 4,536,117 A | * | 8/1985 | Yamashiro | 411/411 |
| 4,600,224 A | * | 7/1986 | Blose | 285/334 |
| 4,810,149 A | * | 3/1989 | Lee et al. | 411/411 |
| 4,863,383 A | * | 9/1989 | Grafelmann | 433/174 |
| 5,662,475 A | * | 9/1997 | Mena | 433/172 |
| 6,315,564 B1 | * | 11/2001 | Levisman | 433/174 |
| 6,843,653 B2 | * | 1/2005 | Carlton | 433/174 |
| 6,997,927 B2 | * | 2/2006 | Jackson | 606/273 |
| 7,198,488 B2 | | 4/2007 | Lang et al. | |
| 7,281,925 B2 | * | 10/2007 | Hall | 433/174 |
| 2003/0197376 A1 | * | 10/2003 | Sivley, IV | 285/333 |
| 2005/0266381 A1 | * | 12/2005 | Abarno | 433/173 |

* cited by examiner

*Primary Examiner* — Todd Manahan
*Assistant Examiner* — Michael R Ballinger

(57) ABSTRACT

A dental implant device for insertion into bone includes an implant anchor having an interlocking thread helically defined around a longitudinal axis, the thread being adapted to couple to a female threaded portion in a bone. The interlocking thread has a first superior contact surface having a first angle relative to the longitudinal axis, a second superior contact surface extending radially outward from the first contact surface and having a second angle relative to the axis, and an inferior flank surface having a third angle relative to the axis. The first angle is larger than the second angle such that the first contact surface and the second contact surface form an approximate "V" or chevron shape in a cross-sectional view. The first angle is larger than the third angle.

1 Claim, 9 Drawing Sheets

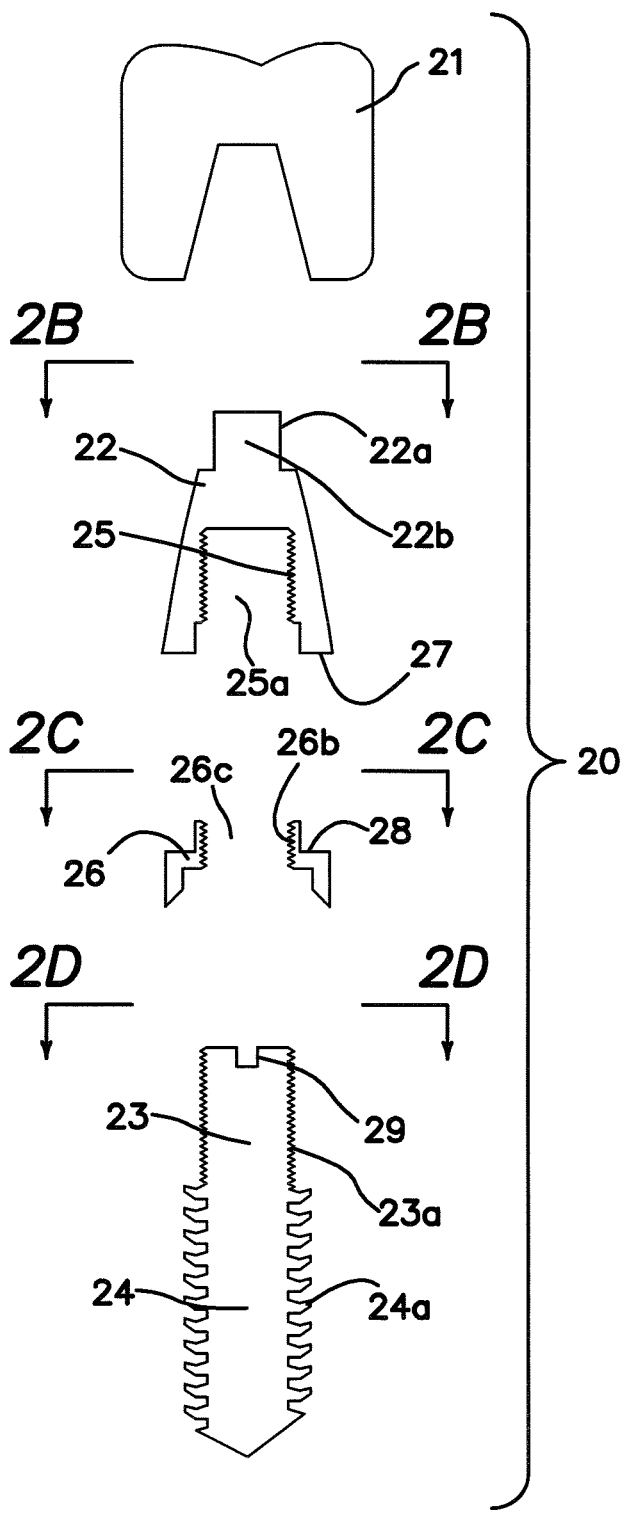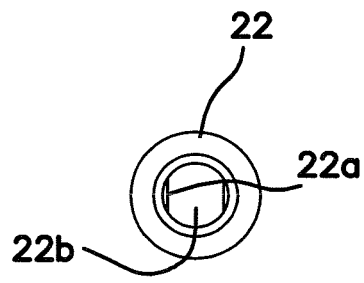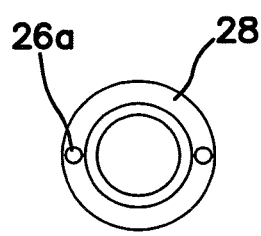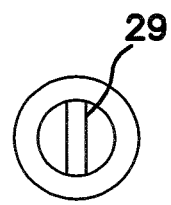
FIG. 2A
FIG. 2B
FIG. 2C
FIG. 2D

DENTAL IMPLANT WITH INTERLOCKING AND CENTERING THREADS

BACKGROUND OF THE INVENTION

1. Field of the Invention

The invention relates generally to dental implant and more particularly to a dental implant anchoring device with threading which does not compress or exert expanding pressure to the surrounding bone.

2. Description of the Prior Art

Dental implants have been used as artificial tooth roots on which prosthetic teeth are mounted. A conventional dental implant 1 shown in FIG. 1 has been described in U.S. Pat. No. 7,198,488. The dental implant 1 has a cylindrical anchoring head 2 formed unitarily with a screw element 3. The screw element 3, usually made of titanium with a roughened surface, is to be screwed into the recipient jaw bone. The anchoring head 2 is adapted to have a prosthetic tooth mounted on it.

The screw element 3 has a thread core 8 and a self-cutting external thread 9. After being anchored into the bone, it may take months for new bone to grow into close proximity with the surface of the screw element 3. Because of a unique property of roughened titanium, newly grown bone can adhere tightly to the surface of the screw element 3.

BRIEF SUMMARY OF THE INVENTION

An illustrated embodiment of the invention is a dental implant device for insertion into bone, comprising an implant anchor having an interlocking thread helically defined around a longitudinal axis. The thread is adapted to couple to a female threaded bore in the bone. The interlocking thread comprises a first superior contact surface having a first angle α relative to the longitudinal axis. The interlocking thread also has a second superior contact surface extending radially outward from the first contact surface and having a second angle β relative to the axis. The first and second contact surfaces form a superior thread surface with a chevron or V shape. An inferior flank surface of the thread having a third angle γ relative to the axis. The first angle α is larger than the second angle β thereby forming the an approximate longitudinally cross-sectional "V" shape. The first angle α is larger than the third angle γ.

In one embodiment the third angle γ is approximately 90 degrees. The first angle α is larger than 90 degrees and the second angle β is smaller than 90 degrees.

The first contact surface is adapted to receive a first force from a female threaded portion of the bone when the implant anchor is tightened into the bone. The first force has a radial component toward the axis. The second contact surface is adapted to receive a second force from a female threaded portion of the bone. The second force has a radial component away from the axis.

The thread further comprises an inferior relief surface intersecting the inferior flank surface and forming an approximate "V" shape in the inferior surface of the thread. The relief surface receives a third force from the female threaded portion of the bone, which third force has a radial component toward the axis.

The second contact surface is adapted to provide a resilient force on the implant anchor for preventing the implant anchor from sliding away from the female threaded portion of the bone.

The thread on the dental implant substantially or generally has a chevron cross-sectional shape.

The dental implant device is used in combination with a prosthetic tooth, and further comprises an abutment adapted to receive the prosthetic tooth; and an opposing collar coupled to the implant anchor which is adapted to provide a support for the abutment when the abutment is mounted on the implant anchor, The opposing collar has a downward-angled surface creating a reaction force when in contact with the bone opposing the reaction force applied to the implant anchor thread to create a clamping force on the bone when the collar is tightened downwardly on the implant anchor against the bone.

In one embodiment a threaded inner bore is defined in the opposing collar and a threaded stem is provided the implant anchor. The opposing collar is threadably coupled to the implant anchor by engagement of the bore with the stem.

In another embodiment the opposing collar is adapted to slide along a threaded stem of the implant anchor through a relatively smooth inner bore in the opposing collar.

In yet another embodiment the abutment is adapted to couple to the implant anchor using an internal female threaded portion in the abutment and a male external threaded stem of the implant anchor.

In still another embodiment abutment is adapted to couple to the implant anchor using a male threaded shaft axially extending from the abutment and a female threaded bore defined in the implant anchor.

The illustrated embodiment also includes a method of implanting a dental implant into a female threaded portion of bone comprising the steps of coupling a male threaded portion of the dental implant to the female threaded portion of bone, and tightening the dental implant to the female threaded portion of bone. The step of tightening the dental implant comprises the step of creating a radially interlocking and centering force between the male threaded portion of the dental Implant and the female threaded portion of the bone.

The step of receiving an interlocking force on the male threaded portion from the female threaded portion comprises the step of receiving a first force on a first contact surface of the male threaded portion from the female threaded portion of bone, the first force having a radial component toward an axis of the dental implant, and receiving a second force on a second contact surface of the male threaded portion from the female threaded portion of bone, the second force having a radial component away from the axis. The first surface and the second surface form an approximately longitudinally cross-sectional "V" shape.

The method further comprises the step of receiving a third force on a third contact surface of the male threaded portion from the female threaded portion of the bone. The third force has a radial component toward the axis.

The method further comprises the step of clamping a downward-angled surface of an opposing collar on the bone.

Still further the illustrated embodiments of the invention include a dental implant device for engaging a female threaded portion of bone, which has means for interlocking with the female threaded portion of bone; and means for adjustably supporting an abutment.

The means for interlocking with the female threaded portion of bone includes a thread having a first contact surface, and a second contact surface forming an approximate, longitudinal cross-sectional "V" shape.

The dental implant device further comprises means for clamping the means for interlocking.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

BRIEF DESCRIPTION OF THE DRAWINGS

FIG. 2a is an exploded side cross-sectional view which shows components of a dental implant device in accordance with an embodiment of the invention employing a threaded collar and an internally thread abutment.

FIG. 2b is a top plan view of the abutment shown in the exploded view of FIG. 2a as seen from section lines 2b-2b in FIG. 2a.

FIG. 2c is a top plan view of the collar shown in the exploded view of FIG. 2a as seen from section lines 2c-2c in FIG. 2a.

FIG. 2d is a top plan view of the anchor shown in the exploded view of FIG. 2a as seen from section lines 2d-2d in FIG. 2a.

FIG. 6 is a side view of the assembled device of FIG. 2a.

FIG. 7b is a top plan view of the shoulder shown in the exploded view of FIG. 7a as seen from section lines 7b-7b in FIG. 7a.

FIG. 7c is a top plan view of the collar shown in the exploded view of FIG. 7a as seen from section lines 7c-7c in FIG. 7a.

FIG. 7d is a top plan view of the anchor shown in the exploded view of FIG. 7a as seen from section lines 7d-7d in FIG. 7a.

FIG. 8 is an assembled side elevational view of the embodiment of FIG. 7a.

FIG. 9b is a top plan view of the shoulder shown in the exploded view of FIG. 9a as seen from section lines 9b-9b in FIG. 9a.

FIG. 9c is a top plan view of the collar shown in the exploded view of FIG. 9a as seen from section lines 9c-9c in FIG. 9a.

FIG. 9d is a top plan view of the anchor shown in the exploded view of FIG. 9a as seen from section lines 9d-9d in FIG. 9a.

FIG. 10 is a side elevational assembled view of the embodiment of FIG. 9a.

Figure 1:
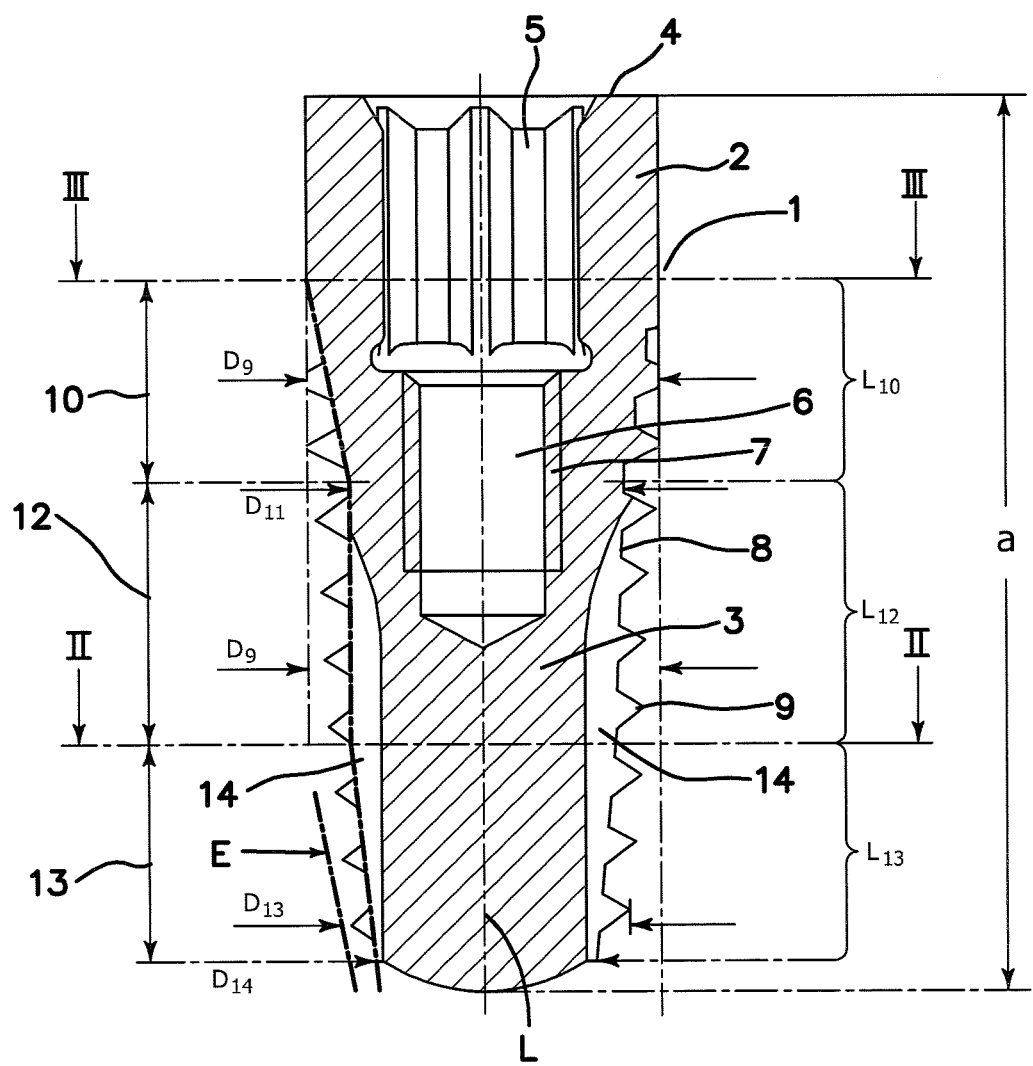
FIG. 1 is a side cross-sectional view which shows a conventional dental implant.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

Conventional dental implants incorporate screws with standard thread profiles such as acme threads, buttress threads, or circumferential groves or even holes drilled through the device into which bone may grow to bind the screw. These implants require regeneration of bone to grow into and around the screw, which can take months, to fully anchor. In addition, conventional implants can weaken the implant site as a result of occlusal processes because of the radial spreading forces transferred from the tooth through the screw to the bone by their thread designs and groove geometries.

The illustrated embodiments of the invention provide an interlocking mechanism for an implant anchor. Through a "chevron" shaped external thread geometry on the screw, the implant anchor becomes interlocked with the receiving hole in the bone immediately upon installation. This results in shorter healing time, simplified procedures, reduced cost and less pain for the patient. The chevron thread not only produces better resistance to shear loads during the occlusal processes, but also adds strength to the implant site. These properties lead to better long-term strength and durability for the implant. The stronger fixation provided by the illustrated embodiments of the invention can produce a better platform for the prosthesis in softer portions of the jaw bone such as in molar areas, and may benefit osteoporotic bone as well, which is often too brittle for standard implants.

FIGS. 2a-2d show a dental implant assembly 20 in accordance with an embodiment of the invention. A prosthetic tooth 21 is arranged and configured to be mounted on a top post 22a of an abutment 22. Although the abutment 22 has a generally conical shape to match mating surfaces defined into tooth 21, the right cylindrical post 22b forming the top of abutment 22 may have flat vertical facets 22a as shown in the top view of FIG. 2b of the abutment 22. This allows a torque to be applied to the abutment 22 on the flat surfaces 22a using a wrench or other tool to facilitate screwing abutment 22 into inferior structures in assembly 20 described below.

Figure 6:
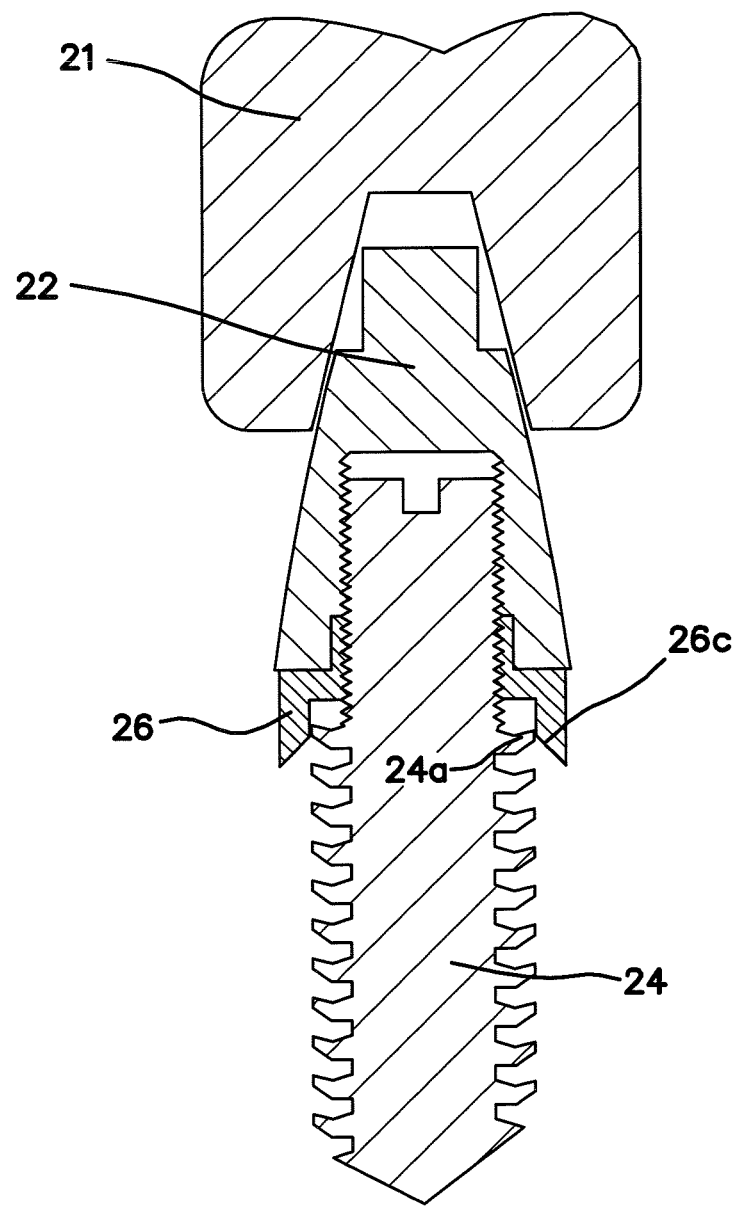
Figure 7A:
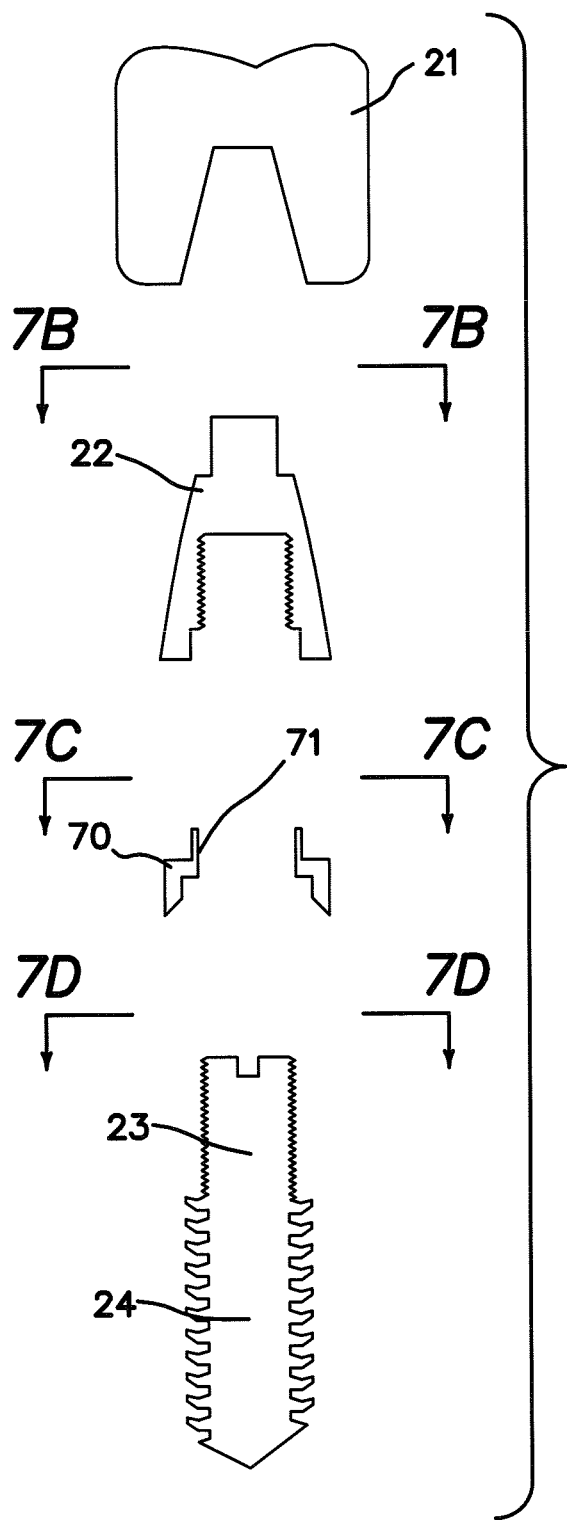
FIG. 7a is an exploded side cross-sectional view of a second embodiment which shows a dental implant device having an adjustable unthreaded collar and an internally thread abutment.
Figure 7B:
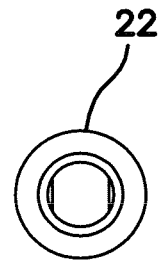
Figure 7C:
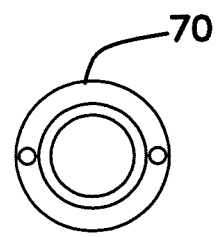
Figure 7D:
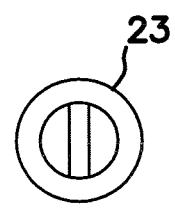

The abutment 22 has an axial bore 25a with an internal thread 25, so that abutment 22 can be threaded onto the external thread 23a of an externally-threaded stem 23 of the implant anchor or screw 24 as best shown in FIG. 6. External threads 23a are arranged and configured to provide mechanical coupling of anchor 24 to collar, also called opposing collar, 26 and abutment 22. Chevron threads 24a are selectively defined in or on the exterior of anchor 24 from or near the lower end of threads 23a to or near the distal end of anchor 24. As shown in FIG. 6, when assembled only chevron threads 24a will be exposed to the bone when implant assembly 20 is completely assembled as intended. Opposing collar 26 is also provided with an axial bore 26c with an internal thread 26b to screwed onto thread 23a and engage threaded stem 23. Collar 26 can be selectively adjusted up or down to aid in the implantation procedure as best shown in FIG. 6. The opposing collar 26 also provides a larger-diameter support base on stepped surface 28 for firm support of the lower stepped surface 27 of abutment 22, which is again best depicted in FIG. 6. The bottom surface 27 of the abutment 22 seats against surface 28 of the opposing collar 26. The opposing collar 26 is tightened onto the externally-threaded stem 23 through internal threads 26b, using a spanner wrench applied to holes 26a defined into surface 28 as best shown in FIG. 2c. The implant anchor 24 is tightened into a receiving female hole formed by the oral surgeon in the jaw bone, which hole has threads matching the external threads 24a. Tightening is performed using driving slot 29 defined in the upper end of the implant anchor 24 as depicted to top plan view in FIG. 2d.

Figure 3:
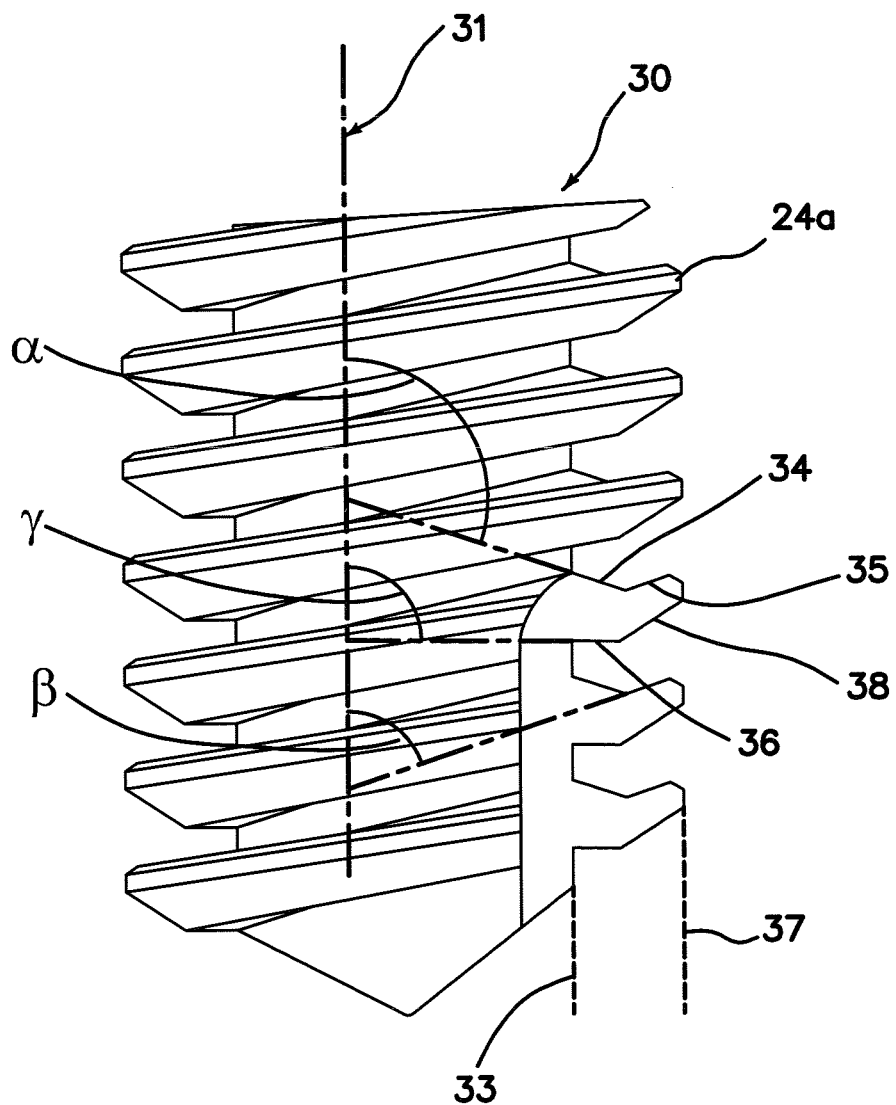
FIG. 3 is a side view of the distal portion of the anchor in enlarged scale which shows a threaded section of the dental implant of the invention, which a lower right partially cut-away side cross-sectional portion.

A distal threaded portion 30 of the implant anchor 24 in accordance with the embodiment of FIGS. 2a-2d is illustrated in enlarged scale in side elevational view in FIG. 3. The threaded section 30 has a generally cylindrical shaped envelope with a longitudinal axis 31. The external thread 24a is defined helically around the circumference of the section 30. The depth of external thread 24a extends between a minor diameter 33 and a major diameter 37 of the threaded section 30.

The external thread 24a has a first superior contact surface 34 and a second more radial superior contact surface 35, an interlocking inferior flank surface 36, and an inferior relief surface 38. When viewed in a side or longitudinal cross-sectional view, the contact surfaces 34 and 35 form an approximate "V" shape, with the flank surface 36 and the relief surface 38 also forming an approximate "V" shape. The thread has an overall "chevron" shape in the cross-sectional view as shown in the partial cut-away side cross-sectional view in the lower right portion of FIG. 3.

Interlocking flank surface 36 forms an angle γ, which in accordance with the embodiment of FIG. 3 is approximately 90 degrees to the axis 31. Contact surface 34 Forms an angle α to the axis 31. The angle α is typically greater than the angle γ, e.g., greater than 90 degrees in the embodiment of FIG. 3. The difference between the first and second angles α and γ, together with the upward-angled surface 35, making an acute angle β with respect to axis 31, provide an interlocking interference of the male threaded section 30 to a female threaded receiving hole formed by the oral surgeon in the bone.

Pullout of anchor 24 from the bone is prevented as a result of the angle of contact surface 34 relative to the angle of contact surface 35. A mirror shaped thread formed in the bone mates with surfaces 34 and 35 of anchor 24, so that the mirror surfaces in the bone are juxtapositioned to surfaces 34 and 35 and substantially prevent or limit any radial movement of anchor 24 relative to the bone. Any attempted radial movement of anchor 24 would tend to cause the outer portion of the thread 24a to move downwardly at the angle β due to the overly bone adjacent to surface 35. However, such movement is blocked or mechanically resisted, because it would tend to drive surface 36 into the opposing juxtapositioned surface of the bone adjacent to surface 36. Hence, anchor 34 is radially locked into place relative to any radial occlusive forces or other forces having a radial component which may be applied to anchor 24. Further, the next lower adjacent thread surface 34 will tend to support the bony material resisting downwardly driven surface 36 in the thread above it, thereby providing a strong backing.

Figure 4:
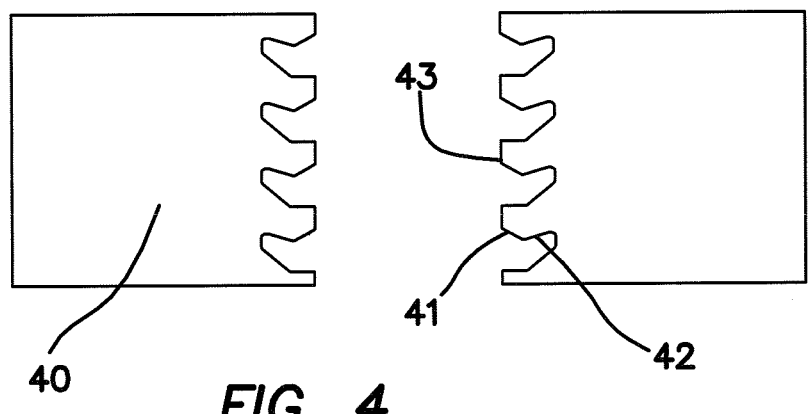
FIG. 4 is a side cross-sectional view of a bone site which shows a female threaded section for receiving the dental implant.

FIG. 4 shows a female threaded portion 40 which is formed in the bone. The female thread teeth 43 are complimentarily shaped to the male thread 24a and has surfaces 41 and 42 corresponding to surfaces 34 and 35, respectively. The female threaded portion 40 of bone is preferably formed by threading a hole with a tap which is the approximate mirror shape the male threads 24a. In the illustrated embodiment, anchor 24 is not self-tapping and hence no substantial radially compressive forces are normally applied to the bone when a pure torque is applied to anchor 24. However, it must be understood that it is entirely within the spirit and scope of the invention that threads 24a could be modified to assume a self-tapping form if desired.

Figure 5:
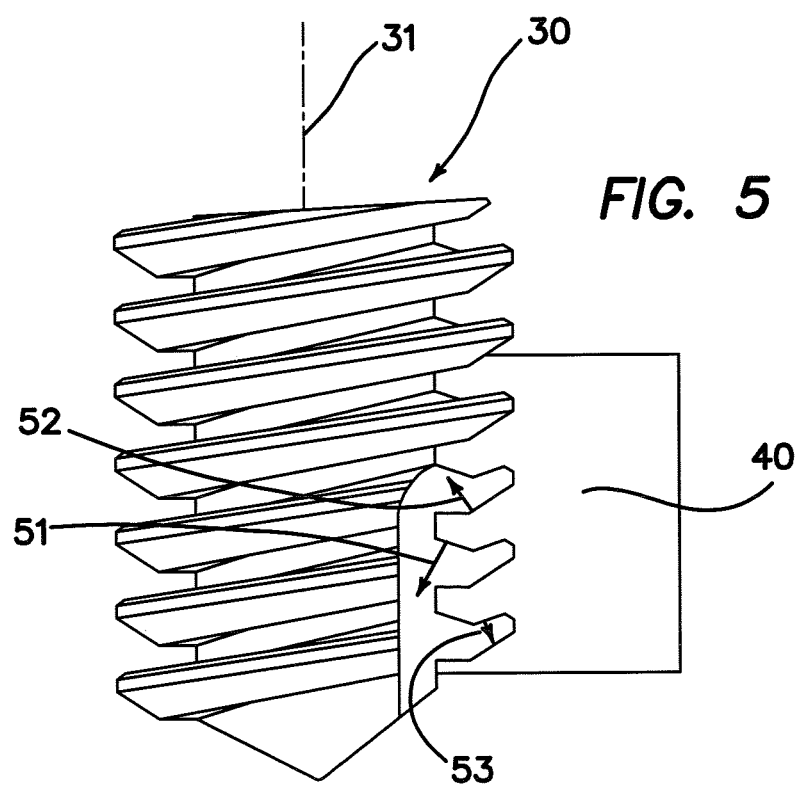
FIG. 5 is a side view of the distal portion of the anchor in enlarged scale which illustrates the reaction forces from the bone applied to the threaded section of the dental implant with a partially cut-away section of the anchor shown in side cross-sectional view coupled to the female threaded section in the bone site as shown in side cross-sectional view.

FIG. 5 is a side elevational view the male threaded portion 30 of FIG. 3 engaged with a side cross-sectional view of the female threaded portion 40 of bone with a partially cut-away section of the anchor 24 shown in side cross-sectional view. In such an engaged state, an interlocking joint is created as described above. As the connection between the male threaded portion 30 and the female threaded portion 40 is tightened, surfaces 34 and 35 bear against surfaces 41 and 42, respectively. A centering force is generated between the female threaded portion 40 and the male threaded portion 30 because of the chevron shape. This centering force is uniformly and helically distributed around the circumference of the mating threads when engaged. This centering force prevents spreading or drawing of the joint between the anchor 24 and the threaded hole in the bone.

A vector reactive force from the bone illustrated as arrow 51 in FIG. 5 acts upon the contact surface 34 of thread 24a by surface 41 of the tapped bone, and a vector reactive force from the bone illustrated as arrow 52 acts upon the surface 38 of thread 24a by means of surface 42 of the tapped bone. Both vector forces 51 and 52 have an inward radial component toward the axis 31, which radial component is determined by the angle of the reactive surfaces and their areas. Similarly, a reactive vector force from the bone represented by arrow 53 acts upon the contact surface 35 of thread 24a by surface 42 of the tapped bone and has an outward radial component away from the axis 31. The vector sum forces 51, 52 and 53 prevent the threaded portion 30 of anchor 24 from radially sliding with respect to the female threaded portion 40 of the tapped bone, or provide a net centering force.

FIG. 6 shows the assembled device 20 with the opposing collar 26 overlying the threads 24a of the implant anchor 24. When tightened, the downward-angled surface 26c of the opposing collar 26 creates a reaction force from the bone which opposes the reaction force from the bone arising from upward-angled thread 24a, thereby creating a longitudinal clamping force.

Figure 8:
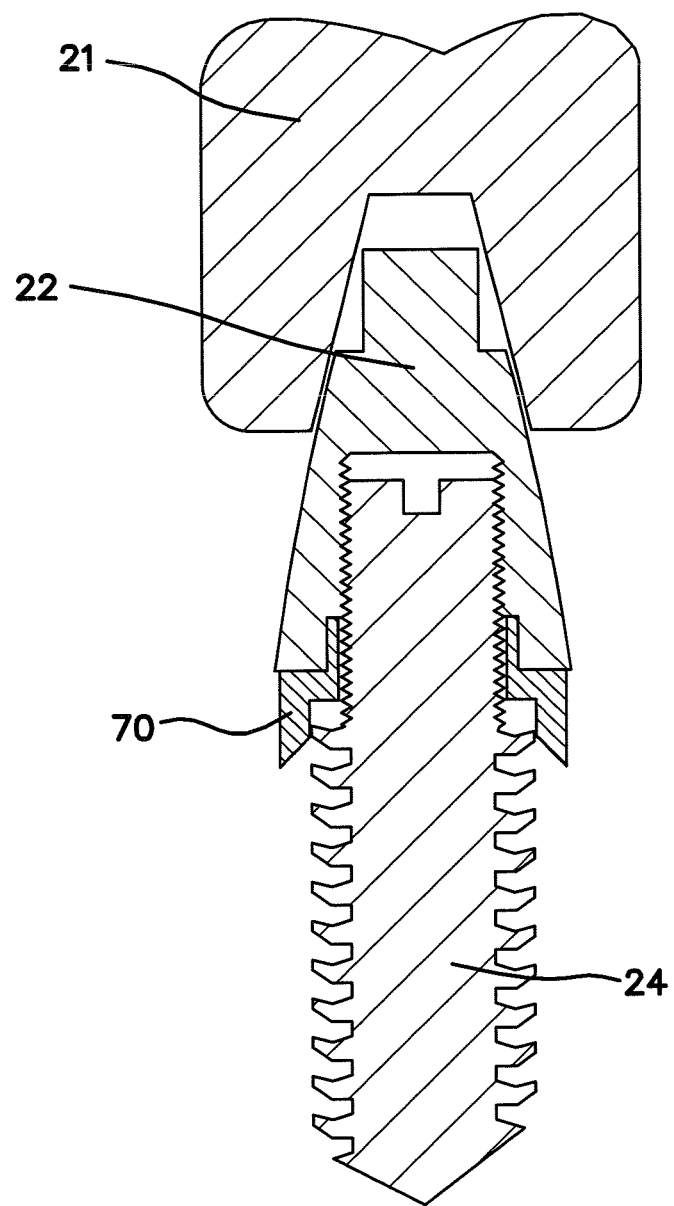
Figure 9A:
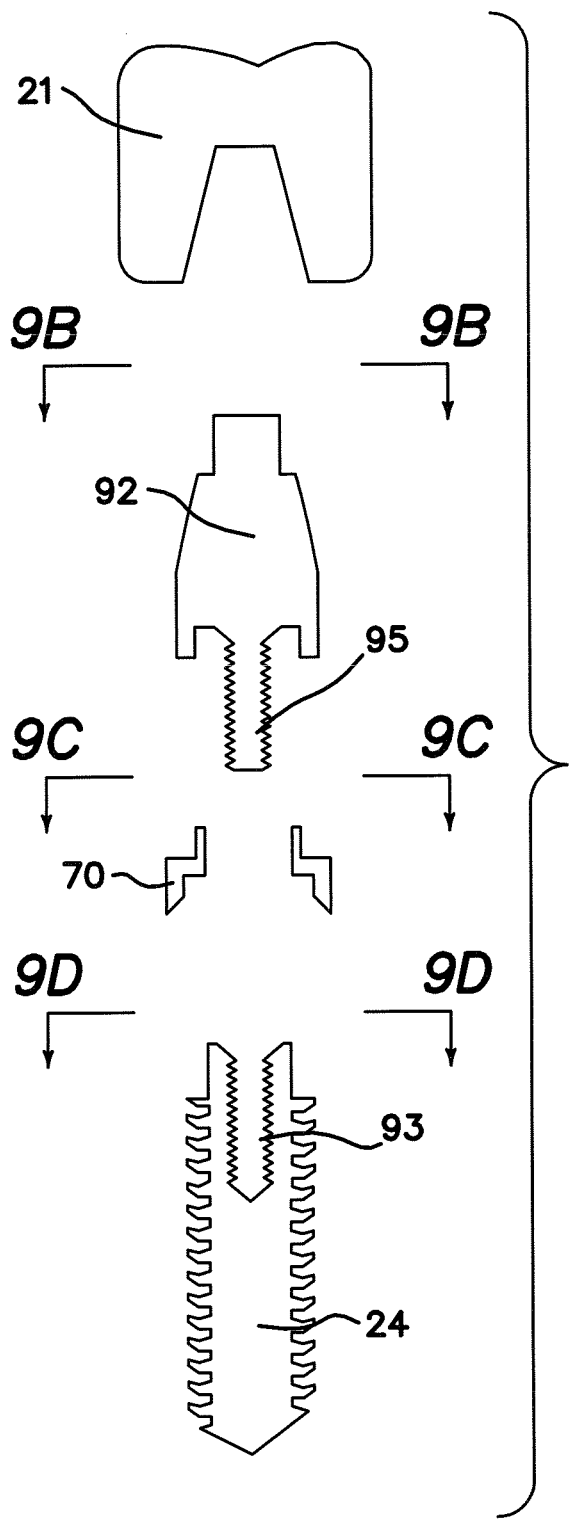
FIG. 9a is an exploded side cross-sectional view of a third embodiment which shows a dental implant device having an adjustable unthreaded collar and an externally threaded shaft extending distally from the abutment.
Figure 9B:
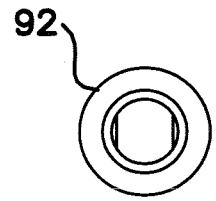
Figure 9C:
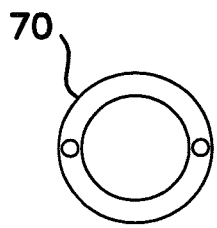
Figure 9D:
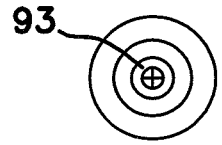

FIGS. 7a-7d show an opposing collar 70 in accordance with another illustrated embodiment of the invention. The embodiment of FIGS. 7a-7d differs from that of FIGS. 2a-2d in that collar 70 has a relatively smooth inner bore 71 without threading. This allows the abutment 22 to force the opposing collar 70 downward as it is threaded onto the threaded portion 23 of the implant anchor 24 creating a clamping force against the bone due to tightening of abutment 22 instead of tightening of collar 70. The assembled view of this device is shown in FIG. 8.

Figure 10:
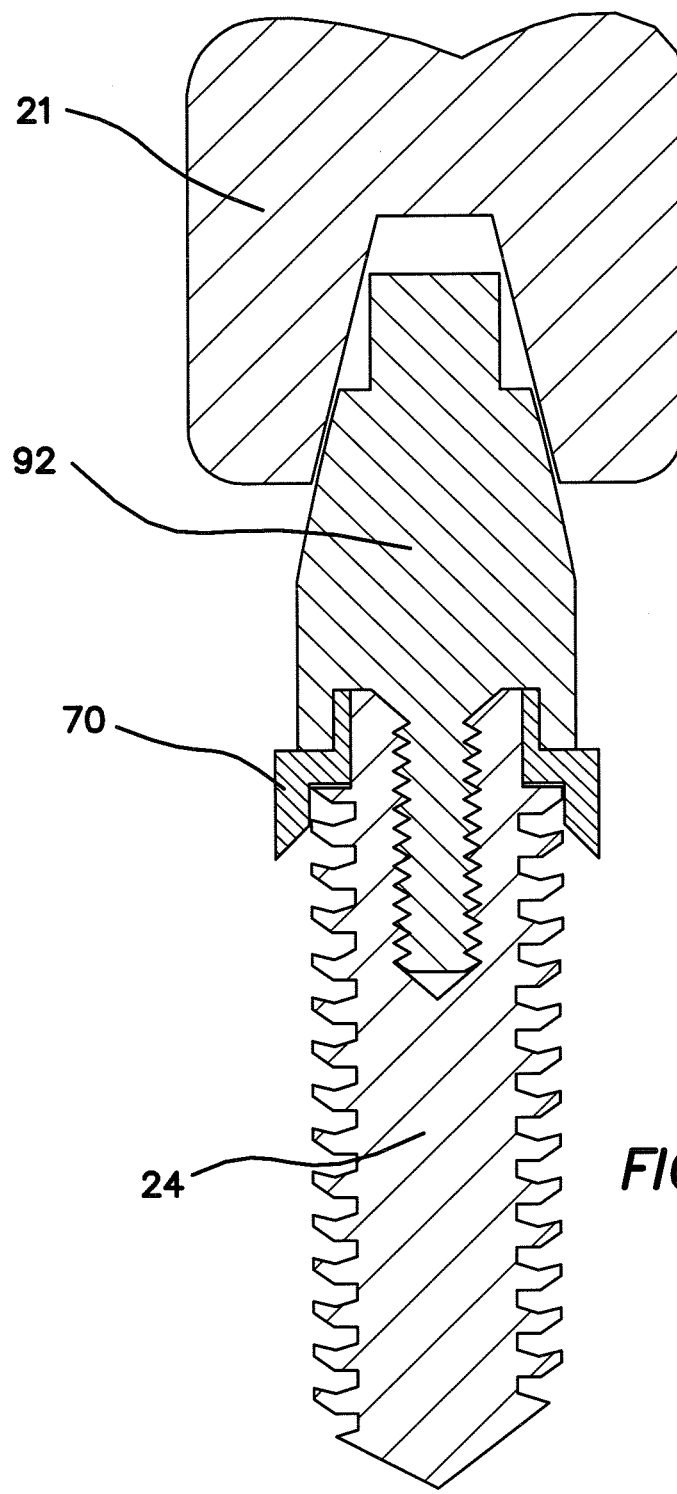

FIGS. 9a-9d are views which show yet another illustrated embodiment where the abutment 92 is provided with a male threaded distal shaft 95 instead of an internal female threaded portion 25 as in the above embodiments. The threaded shaft 95 couples to the implant anchor 24 within an axially defined female threaded hole 93. FIG. 10 is a side cross-sectional view which shows an assembled implant assembly 20 of FIGS. 9a-9d.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments. For example, the thread may not have all of the first contact surface, the second contact surface, the flank surface, and the relief surface, so long as one surface, such as the second surface, provides means for preventing the thread from sliding away from the female threaded portion. On the other hand, more surfaces may be provided. In addition, the surfaces may be angled differently from those shown in the exemplary drawings.

Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

I claim:

1. A bone screw comprising a threaded section wherein threads emanate from a cylindrical shaft, said shaft extending from one thread to an adjacent thread, said threads having two upper facets and two lower facets, all are planar when reviewed in section, said two upper facets and said two lower facets each meeting to form a "V" shape on upper and lower surfaces respectively, the "V" shape on the upper and lower surfaces each oriented in the same direction such that each thread continuously narrows in size as it becomes more radially distant from the shaft.

* * * * *